US007449590B2

United States Patent
Tsuji et al.

(10) Patent No.: US 7,449,590 B2
(45) Date of Patent: Nov. 11, 2008

(54) PROCESS FOR PREPARATION OF PROPYLENE OXIDE

(75) Inventors: Junpei Tsuji, Ichihara (JP); Masaru Ishino, Sodegaura (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 494 days.

(21) Appl. No.: 10/489,955

(22) PCT Filed: Sep. 12, 2002

(86) PCT No.: PCT/JP02/09320

§ 371 (c)(1),
(2), (4) Date: Mar. 18, 2004

(87) PCT Pub. No.: WO03/027087

PCT Pub. Date: Apr. 3, 2003

(65) Prior Publication Data

US 2004/0254386 A1    Dec. 16, 2004

(30) Foreign Application Priority Data

Sep. 21, 2001 (JP) ............................. 2001-288715
Sep. 21, 2001 (JP) ............................. 2001-288716
Sep. 21, 2001 (JP) ............................. 2001-288717

(51) Int. Cl.
*C07D 301/02* (2006.01)
*C07D 301/03* (2006.01)
*C07D 301/19* (2006.01)

(52) U.S. Cl. ..................... 549/518; 549/523; 549/529

(58) Field of Classification Search .............. 549/518, 549/523, 529
See application file for complete search history.

(56) References Cited

U.S. PATENT DOCUMENTS 3,351,635 A * 11/1967 Kollar ..................... 549/529
2002/0151730 A1   10/2002 Oku et al.

FOREIGN PATENT DOCUMENTS

| EP | 170836 B1 | 2/1986 |
| EP | 0 170 836 B1 | 3/1989 |
| EP | 0 673 935 A | 9/1995 |
| WO | WO01/05778 A * | 1/2001 |
| WO | WO 01/05778 A1 | 1/2001 |

OTHER PUBLICATIONS

Chemical Abstracts, vol. 107, No. 8, 1989, Columbus, Ohio (Abstract No. 60993p, XP002351995).

* cited by examiner

*Primary Examiner*—Taylor Victor Oh
(74) *Attorney, Agent, or Firm*—Sughrue Mion, PLLC

(57) ABSTRACT

A process for producing propylene oxide, which comprises the following steps below, and a step for removing alcohols of the carbon number of 2 to 3, cyclohexanol and/or isopropyl-cyclohexane outside of the reaction system in at least one place of the steps or between which the steps are connected:

oxidation step: a step of obtaining cumene hydroperoxide by oxidizing cumene;

epoxidation step: a step of obtaining propylene oxide and cumyl alcohol by reacting cumene hydroperoxide obtained in the oxidation step with propylene in an excess amount in a liquid in the presence of a solid catalyst; and hydrogenolysis step: a step of obtain cumene by subjecting cumyl alcohol obtained in the epoxidation step to hydrogenolysis, and recycling the cumene to the oxidation step as the raw material for the oxidation step.

9 Claims, No Drawings

PROCESS FOR PREPARATION OF PROPYLENE OXIDE

TECHNICAL FIELD

The present invention relates to a process for producing propylene oxide. More particularly, the present invention relates to a process for producing propylene oxide, which has excellent characteristics that propylene is converted into propylene oxide using cumene hydroperoxide obtained from cumene as an oxygen carrier; that the cumene can be used repeatedly; that a reaction volume in each step can be utilized effectively; and that production of unnecessary organic acids and peroxides can be suppressed.

BACKGROUND ART

A process which contains converting propylene into propylene oxide and cumyl alcohol using cumene hydroperoxide obtained by oxidation of cumene, as an oxygen carrier; obtaining cumene by hydrogenolysis of cumyl alcohol; and using the cumene repeatedly, is disclosed in WO 01/05778A, or the like.

DISCLOSURE OF THE INVENTION

According to studies of the present inventors, there was a problem that, in the propylene oxide production described above, the activity of a catalyst deteriorated with passage of time. Regarding it, as results of additional studies, it was found that as one of substances causing retardant of the reaction, organic acids were listed, and in the production, alcohols of the carbon number of 2 to 3, cyclohexanol and isopropylcyclohexane were by-produced and accumulated, and depending on the accumulation thereof, amounts of unnecessary organic acids and peroxides by-produced became large. Oxides cause production of organic acids. Further, it was also found that effective utilization of a reaction volume in each step was damaged by the accumulated components.

The present invention was attained as the results of extensive studies based on findings described above, and an object of the present invention is to provide a process for producing propylene oxide, which has excellent characteristics that the process converts propylene into propylene oxide using cumene hydroperoxide obtained from cumene as an oxygen carrier; that the cumene can be used repeatedly; that reaction volume in each step can be utilized effectively; and that production of unnecessary organic acids and peroxides can be suppressed.

Namely, the present invention relates to a process for producing propylene oxide, which comprises the following steps:

oxidation step: a step of obtaining cumene hydroperoxide by oxidizing cumene;

epoxidation step: a step of obtaining propylene oxide and cumyl alcohol by reacting cumene hydroperoxide obtained in the oxidation step with propylene in an excess amount in a liquid in the presence of a solid catalyst; and hydrogenolysis step: a step of obtain cumene by subjecting cumyl alcohol obtained in the epoxidation step to hydrogenolysis, and recycling the cumene to the oxidation step as a raw material for the oxidation step, wherein the process has a step for removing alcohols of the carbon number of 2 to 3, cyclohexanol and/or isopropylcyclohexane outside of the reaction system in at least one place of the steps or between which the steps are connected.

BEST MODE FOR CARRYING OUT THE INVENTION

The oxidation step in the present invention is a step for obtaining cumene hydroperoxide by oxidation of cumene. The oxidation of cumene is usually effected by autoxidation with oxygen-containing gas such as air, an oxygen-enriched air or the like. The oxidation reaction may be carried out without any additive or with an additive such as an alkali. The reaction temperature is usually 50 to 200° C., and the reaction pressure is usually between the atmospheric pressure and 5 MPa. In the oxidation with the additive, the alkali reagent includes alkali metal compounds such as NaOH and KOH; alkaline earth metal compounds, alkali metal carbonates such as $Na_2CO_3$ and $NaHCO_3$, ammonia, $(NH_4)_2CO_3$, alkali metal ammonium carbonates and the like.

The epoxidation step in the present invention is a step for obtaining propylene oxide and cumyl alcohol by reacting cumene hydroperoxide obtained in the oxidation step with propylene. From viewpoints that the desired product should be obtained in a high yield and under a high selectivity, the epoxidation step is preferably conducted in the presence of a catalyst containing a titanium-containing silicon oxide. The catalyst is preferably a catalyst containing titanium chemically bound to silicon oxide, so-called titanium-silica catalyst. For example, products prepared by supporting a titanium compound on a silica carrier, products in which a titanium compound is compounded with a silicon oxide by a co-precipitation or sol-gel method, or titanium-containing zeolite compounds can be listed.

In the present invention, cumene hydroperoxide used as the raw material for the epoxidation step may be a dilute or thick purification or non-purification product.

The epoxidation reaction is carried out by contacting propylene and cumene hydroperoxide with a catalyst. The reaction may be conducted in a liquid phase using a solvent. The solvent should be a liquid under the reaction temperature and pressure, and substantially inert to the reactants and the products. The solvent may be composed of a substance existing in a solution of the hydroperoxide used. When, for example, cumene hydroperoxide is a mixture with cumene as the raw material, it is also possible to use said material, without adding a solvent in particular, as the solvent. Other useful solvents include monocyclic aromatic compounds (e.g. benzene, toluene, chlorobenzene, o-dichlorobenzene), alkanes (e.g. octane, decane, dodecane) and the like.

The epoxidation temperature is generally 0 to 200° C. and preferably 25 to 200° C. The pressure may be any pressure sufficient to keep liquid state of the reaction mixture. Generally, the pressure is advantageously 100 to 10,000 kPa.

The epoxidation can advantageously be carried out with a catalyst in the form of a slurry or a fixed-bed. The fixed-bed is preferred in the case of a large-scale industrial operation. In addition, the reaction can be carried out by a batch process, a semi-continuous process, a continuous process or the like. When a liquid containing the raw materials for reaction is passed through a fixed-bed, the catalyst is not contained at all or substantially in a liquid mixture discharged from the reaction zone.

The hydrogenolysis step in the present invention is a step in which cumyl alcohol obtained in the epoxidation step is subjected to hydrogenolysis to obtain cumene, and said cumene is recycled to the oxidation step as the raw material for the oxidation step. In other words, the same product, i.e. cumene used in the oxidation step is recovered. The hydrogenolysis is usually carried out by contacting cumyl alcohol and hydrogen with a catalyst. The reaction may be conducted in a liquid phase using a solvent or in a gas phase. The solvent should be substantially inert to the reactants and the products. The solvent may be composed of a substance existing in a solution of the cumyl alcohol used. When, for example, cumyl alcohol is a mixture with cumene as the product, it is also possible to use said material, without adding a solvent in particular, as the solvent. Other useful solvents include alkanes (e.g. octane, decane, dodecane), monocyclic aromatic compounds (e.g. benzene, ethylbenzene, toluene), and the like. The hydrogenolysis temperature is generally 0 to 500° C. and preferably 30 to 400° C. Generally, the pressure is advantageously 100 to 10,000 kPa. The hydrogenolysis can advantageously be carried out using a catalyst in the form of a slurry or a fixed-bed.

As the catalyst, any catalyst having a hydrogenation ability can be used. Examples of the catalyst include metal catalysts of metals of the groups 9th and 10th of the Periodic Table (Revised edition of IUPAC Inorganic Chemistry Nomenclature 1989) such as cobalt, nickel and palladium and metal catalysts of metals of the groups 11th and 12th metals such as copper and zinc. Copper catalysts are preferred from the viewpoint that by-products are suppressed. The copper catalysts include copper, Raney copper, copper-chromium, copper-zinc, copper-chromium-zinc, copper-silica, copper-alumina and the like. In addition, the reaction can be carried out by a batch process, a semi-continuous process, or a continuous process. When a liquid containing the raw materials for reaction is passed through a fixed-bed, the catalyst is not contained at all or substantially in a liquid mixture discharged from the reaction zone.

In the present invention, a step for removing at least one selected from the group consisting of alcohols of the carbon number of 2 to 3, isopropylcyclohexane and cyclohexanol outside of the reaction system is set up.

When the step for removing the alcohols of the carbon number of 2 to 3 outside of the reaction system (herein after, sometimes referred to as "alcohol removing step") is set up, the step for removing alcohols of the carbon number of 2 to 3 outside of the reaction system in at least one place of the oxidation step, epoxidation step and hydrolysis step steps or between which the steps are connected, is set up. As the alcohols of the carbon number of 2 to 3, ethanol, isopropanol and n-propanol can be listed. These compounds are produced by decomposition of an organic peroxide or successive reactions of propylene oxide. Since the alcohols are components which are accumulated in the system, the concentrations thereof increase with passage of time if the recycle is continued. This causes not only a decrease in effective reaction volume in each of the steps, but also an inconvenience such that organic acids are produced by oxidation of a part thereof, they act as an inhibitor of the epoxidation catalyst and exist as impurities in propylene oxide as product. When the alcohol removing step is set up, the step can be usually carried out by installation of a distillation column or an extracting column in at least one place of the oxidation step, the epoxidation step and the hydrogenolysis step or between these steps connected, or the like.

Further, in the present invention, when the step for removing isopropylcyclohexane is set up, it is preferable to control the concentration of isopropylcyclohexane in cumene recycled from the hydrogenolysis step to the oxidation step to 5% by weight or lower. Isopropylcyclohexane is a compound produced by nuclear hydrogenation of cumene in the hydrogenolysis step. Since isopropylcyclohexane is a component which is accumulated in the system, the concentration thereof increases with passage of time if the recycle is continued, and this causes not only a decrease in effective reaction volume in each of the steps, but also an inconvenience such that organic acids or peroxides are produced by oxidation of a part thereof in the oxidation step.

Considering the effective utilization of the reaction volume and suppression of the by-products, it is preferable to control the concentration of isopropylcyclohexane in cumene recycled to the oxidation step to 5% by weight or lower.

As a method of suppressing the concentration of isopropylcyclohexane, a method of removing whole or a part of isopropylcyclohexane outside of the system of the steps in the present invention by distillation, extraction or the like, a method of converting into another compound by reaction, and a method of reducing the concentration by an absorbent or the like, in addition to a method of selecting hydrogenolysis conditions under which nuclear hydrogenation is difficult to proceed, are exemplified.

In a case of removing outside of the system, the step of removing isopropylcyclohexane (herein-after, sometimes referred to as "isopropylcyclohexane removing step") can be usually conducted by installing a distillation column or extraction column, or the like, in at least one place of the oxidation step, epoxidation step and hydrogenolysis step steps or between which the steps are connected, but it is preferable from viewpoint of suppression at low level of concentrations of by-products and lowering losses of effective components to conduct removal by means of distillation before the oxidation step.

Furthermore, in the present invention, when the step for removing cyclohexanol is set up, it is preferable to control the concentration of cyclohexanol in cumene recycled from the hydrogenolysis step to the oxidation step to 5% by weight or lower. Cyclohexanol is a compound produced by nuclear hydrogenation of phenol in the hydrogenolysis step. Phenol is a compound produced by decomposition of cumene hydroperoxide mainly in the epoxidation step.

Since cyclohexanol is a component which is accumulated in the system, the concentration thereof increases with passage of time if the recycle is continued, and this causes not only a decrease in effective reaction volume in each of the steps, but also an inconvenience such that organic acids are produced by oxidation of a part thereof in the oxidation step.

Considering the effective utilization of the reaction volume and suppression of the by-products, it is preferable to control the concentration of cyclohexanol in cumene recycled to the oxidation step to 5% by weight or lower.

As a method of suppressing the concentration of cyclohexanol, there are exemplified a method of removing whole or a part of cyclohexanol outside of the system of the steps in the present invention by distillation, extraction or the like, a method of converting into another compound by reaction, and a method of reducing the concentration by an absorbent or the like, in addition to a method of selecting hydrogenolysis conditions under which nuclear hydrogenation is difficult to proceed.

In a case of removing outside of the system, the step of removing cyclohexanol (herein-after, sometimes referred to as "cyclohexanol removing step") can be usually conducted by installing a distillation column or extraction column, or the like, in at least one place of the oxidation step, epoxidation step and hydrogenolysis step or between which the steps are connected, but it is preferable from viewpoint of suppression at low level of concentrations of by-products and lowering losses of effective components to carry out removal by means of distillation before the oxidation step.

In the present invention, the reaction effective volume in each of the steps can be reduced by installing any one of the step for removing alcohols of the carbon number of 2 to 3 outside of the system, the step for removing isopropylcyclohexane outside of the system and the step for removing cyclohexanol outside of the system, in addition, the reaction effective volume in each of the steps can be further reduced the installation of at least two of these steps. Moreover, the removal of alcohols of the carbon number of 2 to 3 and cyclohexanol can suppress production of unnecessary organic acids and the removal of isopropylcyclohexane can suppress production of unnecessary organic acids and peroxides.

Furthermore, in the present invention, when at least two of the above-described by-products are removed, variations such as separate installation of respective removal steps for the by-products, installation of one removal step for removing two of the by-products, installation of one removal step for removing three of the by-products, installation of one removal step regarding two by-products among three by-products, or the like, are possible. When one step regarding the by-products of two or more, is used, for example, it is possible to remove together the by-products by distillation, or separately each of the by-products by fractional distillation.

EXAMPLE

Example 1

Oxidation Step

Cumene recycled from a hydrogenolysis step is mixed with air and reacted for 5 hours under conditions of a pressure of 300 kPa at a temperature of 150° C. (the concentration of ethylbenzene in a solution containing cumene recycled to an oxidation step is lower than 10% by weight).

An oxidized liquid produced has the following composition.

Oxidized Liquid Composition

| | |
|---|---|
| Cumene hydroperoxide | 35% by weight |
| Cumyl alcohol | 2% by weight |
| Cumene | 60% by weight |
| Alcohols having 2 to 3 carbons | 0.03% by weight |
| Isopropylhexane | 0.01% by weight |
| Cyclohexanol | 0.01% by weight |
| Others | the balance |

Epoxidation Step

An oxidized liquid obtained in the oxidation step is continuously passed through a fixed bed flow reactor in the presence of a titanium-containing silicon oxide catalyst together with propylene of 10 times by mole to 1 mole of cumene hydroperoxide contained in the washed oxidized liquid. The conversion of cumene hydroperoxide is kept 99% and the reaction system is steady-stabilized by controlling an inlet temperature. At this time, the reaction temperature is 60° C. and the selectivity is 95%. Further, light boiling components are separated and removed from an epoxidized liquid obtained.

A composition of a reaction liquid obtained become as follows:

| Epoxidized liquid composition | |
|---|---|
| Cumene hydroperoxide | 0.4% by weight |
| Cumyl alcohol | 33.5% by weight |
| Isoprpylbenzene | 62.3% by weight |

| -continued | |
|---|---|
| Epoxidized liquid composition | |
| Alcohols having 2 to 3 carbons | 0.02% by weight |
| Isopropyl hexane | 0.01% by weight |
| Cyclohexanol | 0.01% by weight |
| Others | the balance |

Hydrogenolysis Step

The reaction liquid obtained in the epoxidation step is continuously passed through a fixed bed flow reactor in the presence of a copper-chromium catalyst together with hydrogen of 2 times by mole to one mol of cumyl alcohol contained in the reaction liquid. Almost 100% of cumyl alcohol is converted by controlling an inlet temperature. At this time, the reaction temperature is 180° C. A composition of a reaction liquid obtained become as follows:

| Hydrogenolysis liquid composition | |
|---|---|
| Cumene hydroperoxide | 0% by weight |
| Cumyl alcohol | 0% by weight |
| Isoprpylbenzene | 96.1% by weight |
| Alcohols having 2 to 3 carbons | 0.40% by weight |
| Isopropyl hexane | 0.05% by weight |
| Cyclohexanol | 0.15% by weighti |
| Others | the balance |

Step of Removing Alcohols Having 2 to 3 Carbons, Isopropyl Hexane and Cyclohexanol Alcohols having 2 to 3 carbons, isopropyl hexane and cyclohexanol are removed from the hydrogenolysis liquid obtained by hydrogenolysis.

The composition of an oil layer obtained become as follows:

| Hydrogenolysis liquid composition | |
|---|---|
| Cumene hydroperoxide | 0% by weight |
| Cumyl alcohol | 0% by weight |
| Isoprpylbenzene | 96.6% by weight |
| Alcohols having 2 to 3 carbons | 0.00% by weight |
| Isopropyl hexane | 0.01% by weight |
| Cyclohexanol | 0.01% by weight] |
| Others | the balance |

Comparative Example 1

When oxidation, epoxidation and hydrogenolysis are carried out in the same conditions as in Example 1 except that removal of alcohols having 2 to 3 carbons, isopropyl hexane and cyclohexanol is not carried out, the concentration of ethylbenzene in the oil layer which is recycled, continuously increases, and the total concentrations of ethylbenzene, alcohols having 2 to 3 carbons, isopropyl hexane and cyclohexanol contained in a solution containing cumene recycled to the oxidation step, exceed 50% by weight after recycles of 100 times, and effective utilization of the reaction volume in each of steps, becomes impossible. Further, production of unnecessary organic acids becomes larger.

INDUSTRIAL APPLICABILITY

According to the present invention, there can be provided a process for producing propylene oxide, which has excellent characteristics that the process converts propylene into propylene oxide using cumene hydroperoxide obtained from cumene as an oxygen carrier; that the cumene can be used repeatedly; and further that reaction volume in each step can be utilized effectively and production of unnecessary organic acids and peroxides can be suppressed.

The invention claimed is:

1. A process for producing propylene oxide, which comprises the following steps below, and a step for removing alcohols of the carbon number of 2 to 3, cyclohexanol and/or isopropylcyclohexane as by-products outside of the reaction system in at least one place of the steps or between which the steps are connected:

oxidation step: a step of obtaining cumene hydroperoxide by oxidizing cumene;

epoxidation step: a step of obtaining propylene oxide and cumyl alcohol by reacting cumene hydroperoxide obtained in the oxidation step with propylene in an excess amount in a liquid in the presence of a titanium-containing silicon oxide catalyst; and hydrogenolysis step: a step of obtain cumene by subjecting cumyl alcohol obtained in the epoxidation step to hydrogenolysis, and recycling the cumene to the oxidation step as a raw material for the oxidation step.

2. The process according to claim 1, wherein the alcohol compounds of the carbon number of 2 to 3 are removed outside of the reaction system.

3. The process according to claim 1, wherein cyclohexanol and/or isopropylcyclohexane is removed outside of the reaction system.

4. The process according to claim 3, wherein isopropyl cyclohexane is removed outside of the reaction system.

5. The process according to claim 3, wherein cyclohexanol is removed outside of the reaction system.

6. The process according to claim 1, wherein the alcohols of the carbon number of 2 to 3, cyclohexanol and isopropylcyclohexane are removed outside of the reaction system.

7. The process according to claim 1 or 2, wherein the alcohols of the carbon number of 2 to 3 are ethanol, isopropanol and n-propanol.

8. The process according to claim 1 or 4, wherein the concentration of isopropyl cyclohexane in cumene recycled from the hydrogenolysis step to the oxidation step is 5% by weight or lower.

9. The process according to claim 1 or 4, wherein the concentration of cyclohexanol in cumene recycled from the hydrogenolysis step to the oxidation step is 5% by weight or lower.

* * * * *